United States Patent
Moreau et al.

(10) Patent No.: US 11,123,126 B2
(45) Date of Patent: Sep. 21, 2021

(54) UNIVERSAL ADAPTOR FOR GAS SCAVENGING SYSTEMS

(71) Applicant: Medtronic CryoCath LP, Toronto (CA)

(72) Inventors: Stephane Moreau, Blainville (CA); Rachid Mahrouche, La Salle (CA); Eric Monger, Beloeil (CA); Nadine Nahoul, Saint-Laurent (CA); Vladimir Tzonev, Kirkland (CA)

(73) Assignee: Medtronic CryoCath LP

( * ) Notice: Subject to any disclaimer, the term of this patent is extended or adjusted under 35 U.S.C. 154(b) by 97 days.

(21) Appl. No.: 16/593,298

(22) Filed: Oct. 4, 2019

(65) Prior Publication Data

US 2020/0030017 A1 Jan. 30, 2020

Related U.S. Application Data

(63) Continuation of application No. 14/488,871, filed on Sep. 17, 2014, now Pat. No. 10,463,417.

(51) Int. Cl.

| | |
|---|---|
| *A61B 18/02* | (2006.01) |
| *F16L 25/14* | (2006.01) |
| *F16L 33/00* | (2006.01) |
| *A61M 39/10* | (2006.01) |
| *A61B 17/00* | (2006.01) |

(Continued)

(52) U.S. Cl.
CPC ......... *A61B 18/02* (2013.01); *A61M 39/1011* (2013.01); *F16L 25/14* (2013.01); *F16L 33/00* (2013.01); *A61B 2017/00486* (2013.01); *A61B 2018/00172* (2013.01); *A61B 2018/00577* (2013.01); *A61B 2018/0212* (2013.01); *A61B 2018/0268* (2013.01); *F16L 33/30* (2013.01)

(58) Field of Classification Search
CPC . F16L 25/14; F16L 33/00; F16L 33/30; A61B 18/02; A61B 2017/00486; A61B 2018/00172
See application file for complete search history.

(56) References Cited

U.S. PATENT DOCUMENTS

| | | |
|---|---|---|
| 2,086,276 A | 7/1937 | Lindas |
| 2,685,459 A | 8/1954 | Panagrossi |

(Continued)

FOREIGN PATENT DOCUMENTS

WO 2013132086 A1 9/2013

*Primary Examiner* — Matthew Troutman
*Assistant Examiner* — Fannie C Kee
(74) *Attorney, Agent, or Firm* — Christopher & Weisberg, P.A.

(57) ABSTRACT

An adapter for putting two incompatible medical systems in fluid communication with each other. The adapter may have a continuous outer diameter and may include two segments: a first segment composed of a rigid material and including a first portion and a second portion, the first portion having a continuous outer diameter and the second portion defining one or more flanges, the first segment defining a first passage therethrough; and a second segment composed of a flexible material and coupled to the first segment, including a first portion and a second portion. The first portion of the second segment may have an inner surface configured to surround the flanges of the second portion of the first segment, and the second portion of the second segment having a tapered inner surface, the second segment defining a second passage therethrough that is continuous with the first passage.

13 Claims, 5 Drawing Sheets

(51) Int. Cl.
 *F16L 33/30* (2006.01)
 *A61B 18/00* (2006.01)

(56) References Cited

U.S. PATENT DOCUMENTS

| | | |
|---|---|---|
| 3,895,829 A | 7/1975 | Manson, Jr. |
| 4,046,479 A | 9/1977 | Paley |
| 4,675,007 A | 6/1987 | Terry |
| 4,714,279 A | 12/1987 | Custeau |
| 5,123,840 A | 6/1992 | Nates |
| 5,176,415 A | 1/1993 | Choksi |
| 5,370,426 A | 12/1994 | Meyers |
| 5,536,258 A | 7/1996 | Folden |
| 6,916,248 B1 | 7/2005 | Burgess |
| 7,458,613 B2 | 12/2008 | Spears |
| 7,527,302 B2 | 5/2009 | Lewis et al. |
| 2003/0230894 A1 | 12/2003 | Cleveland et al. |
| 2004/0155459 A1 | 8/2004 | Katayama et al. |
| 2005/0067833 A1 | 3/2005 | Ball |
| 2006/0279081 A1 | 12/2006 | Liao |
| 2011/0077910 A1 | 3/2011 | Lim et al. |
| 2013/0150671 A1 | 6/2013 | Levy et al. |

UNIVERSAL ADAPTOR FOR GAS SCAVENGING SYSTEMS

CROSS-REFERENCE TO RELATED APPLICATION

This application is a continuation of and claims priority to U.S. patent application Ser. No. 14/488,871, filed Sep. 17, 2014, entitled UNIVERSAL ADAPTOR FOR GAS SCAVENGING SYSTEMS, the entirety of which is incorporated herein by reference.

FIELD

The present invention relates to a device for putting two incompatible systems in fluid communication with each other. For example, the present invention relates to a universal connecting device to connect the hose of a cryotreatment system to a scavenging outlet of a medical facility, regardless of the configuration of the outlet and/or the geographic area in which the medical facility is located.

BACKGROUND

Cryoablation, the process of killing tissue using extreme cold, is a commonly used technique for treating many medical conditions, particularly those relating to cardiac arrhythmia. During cryoablation, a liquid refrigerant is circulated from a fluid source to a treatment element of a medical device, at which point the refrigerant may expand and cause a reduction in the temperature of the treatment element. For example, liquid refrigerant may be delivered to a balloon of a cryoablation device, and the balloon may have a larger volume than the one or more conduits of the fluid flow path by which the refrigerant is delivered. The liquid refrigerant may expand when it is injected into the balloon, causing a temperature reduction by the Joule-Thomson effect.

Once the refrigerant has expanded within the treatment element, the gaseous refrigerant must be removed from the treatment element and either reclaimed or vented to the atmosphere. For example, the medical device may also be in fluid communication with a vacuum or scavenging system for the recovery of the expanded refrigerant. Typically, a medical facility may include one or more scavenging system outlets built into the walls of the facility. However, the outlet may have any of a variety of configurations, depending on the country or geographic origin in which the facility is located. As a result, a cryoablation console must be specially adapted for each country in which the console is used. For example, a hose that is part of a console's gas scavenging system may be matably connectable to a United States scavenging outlet, but not to an Asian scavenging outlet. Predictably, this increases the cost and difficulty of using a single console in a variety of geographic locations.

Additionally, cryoablation systems are not the only scenario in which compatibility problems may arise. Specialty adapters frequently have to be adapted in other types of facilities, such as automechanics garages, laboratories, and water distribution systems. Like cryoablation systems, it is costly and inefficient to develop and use a plethora of hose or conduit adapters to connect to an incompatible fluid system.

Therefore, it would be desirable to provide a universal adapter that could be used to fluidly connect a hose or conduit, or other component, to any of a variety of system outlets without the need for a specialized adapter for each outlet type or configuration.

SUMMARY

The present invention advantageously provides a method and device for putting two incompatible systems in fluid communication with each other. For example, the present invention relates to a universal connecting device to connect the hose of a cryotreatment system to a scavenging outlet of a medical facility, regardless of the configuration of the outlet and/or the geographic area in which the medical facility is located. In one embodiment, a universal adapter for a medical system may include a first segment composed of a rigid material and defining one or more flanges and a second segment composed of a flexible material, the second segment being coupled to the first segment with at least a portion of the second segment being disposed about the one or more flanges of the first segment. The second segment may include a continuous outer diameter, and each of the first segment and the second segment includes a first portion and a second portion. The second portion of the first segment may include the one or more flanges and a continuous inner diameter. The first portion of the first segment may include a plurality of inner diameters and at least a portion of the first portion may have a threaded inner diameter. Further, the first portion of the second segment may abut the second portion of the first segment. The first portion of the second segment may include a plurality of inner diameters. The second portion of the second segment may have a tapered inner diameter. For example, the second portion of the second segment may have an inner diameter that increases from a first end to a second end of the second portion. The first portion of the second segment may also have a first end and a second end, with at least one of the plurality of inner diameters at the first end of the second portion being at least substantially the same as an inner diameter at the second end of the first portion. The first portion of the second segment may also include a plurality of inner diameters. The first portion of the second segment may be at least partially disposed about the one or more flanges of the first segment.

In another embodiment, a universal adapter for a medical system may include: a first segment composed of a rigid material and including a first portion and a second portion, the first portion having a continuous outer diameter and the second portion defining one or more flanges; and a second segment composed of a flexible material and including a first portion and a second portion, the second segment having a continuous outer diameter that is the same as the continuous outer diameter of the first portion of the first segment, the first portion and the second portion of the second segment each including a plurality of inner diameters, the first segment and the second segment being coupled to each other such that at least a portion of the first portion of the second segment surrounds the one or more flanges of the second portion of the first segment. Each of the first segment and the second segment may define a passage therethrough. At least a portion of an inner surface of the first portion of the first segment may be threaded. The plurality of inner diameters in the first portion of the second segment may be configured to surround the one or more flanges of the second portion of the first segment. Further, the plurality of inner diameters in the second portion of the second segment may increase from a first end to a second end of the second portion of the second segment.

An adapter for a medical system may include: a first segment composed of a rigid material and including a first portion and a second portion, the first portion having a continuous outer diameter and the second portion defining one or more flanges, the first segment defining a first passage therethrough; and a second segment coupled to the first segment and composed of a flexible material and including a first portion and a second portion, the second segment having a continuous outer diameter that is the same as the continuous outer diameter of the first portion of the first segment, the first portion of the second segment having an inner surface that is configured to surround the one or more flanges of the second portion of the first segment, and the second portion of the second segment having a tapered inner surface, the second segment defining a second passage therethrough that is continuous with the first passage of the first segment, the adapter being configured to put a cryotreatment system in fluid communication with an incompatible fluid scavenging system of a medical facility. The first segment of the adapter may be coupled to at least a portion of the cryotreatment system and the second segment of the adapter may be coupled to at least a portion of the fluid scavenging system of the medical facility.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
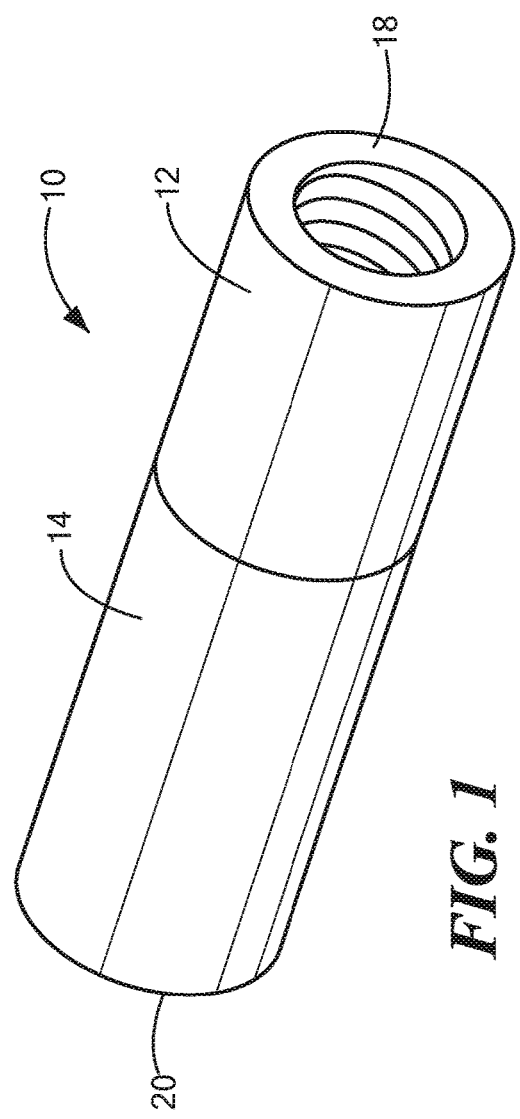
FIG. 1 shows a perspective view of an adapter device.

Referring now to FIGS. 1-5, an adapter device is shown. The adapter device 10 (which also may be referred to as a "universal adapter") may include a flanged segment 12 and a conical segment 14. Further, the adapter device 10 may define a passage 16 between a first device end 18 in the flanged segment 12 and a second device end 20 in the conical segment 14, and the passage 16 may lie along the device's longitudinal axis 22. The passage 16 may mean that both segments 12, 14 may be broadly referred to as being at tubular. The first device end 18 may be the same as the first end 18 of the flanged segment 12 and the second device end 20 may be the same as the second end 20 of the conical segment 14. The flanged segment 12 may be composed of a rigid material, such as plastic or metal, and the conical segment 14 may be composed of a flexible material, such as silicon or similar materials.

Each segment 12, 14 may be manufactured individually and then assembled together, either removably or permanently. For example, the flexible conical segment 14 may fit over the one or more flanges 24 in the flanged segment 12. As described in more detail below, the inner surface 26 of the conical segment 14 may include one or more indentations or channels 28, each one being sized and configured to accept a flange 24 within. The flexible material from which the conical segment 14 is manufactured, plus the configurations of the flanged segment 12 and the inner surface 26 of the conical segment 14, may create a strong matable connection between the segments 12, 14. As such, use of a permanent means of attachment, such as an adhesive, bonding agent, or other method or material, may be unnecessary. However, it will be understood that the segments 12, 14 may be permanently attached to each other by means known in the art. The one or more flanges 24 of the flanged segment 12 and the complementary shape of the inner surface 26 of the conical segment 14 may help "lock" the two segments 12, 14 together without the use of a permanent attachment means, and may strengthen the bond between the segments 12, 14 when a permanent attachment means is used.

Figure 2:
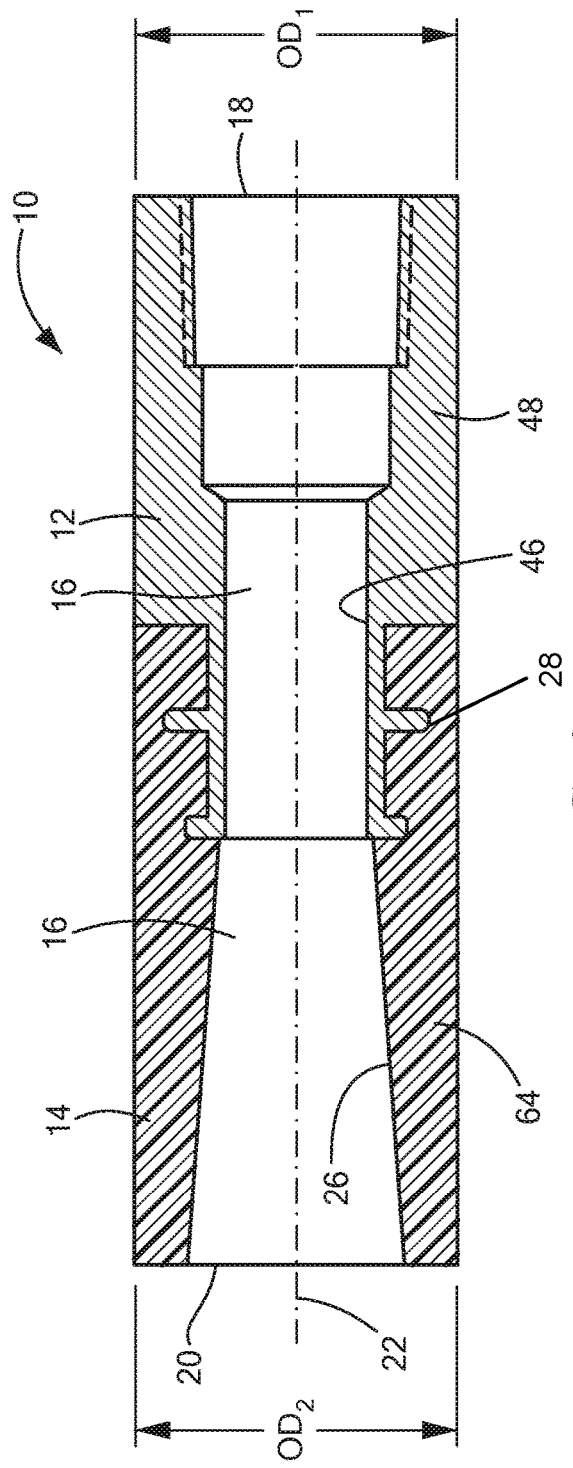
FIG. 2 shows a cross-sectional view of the adapter device.
Figure 3:
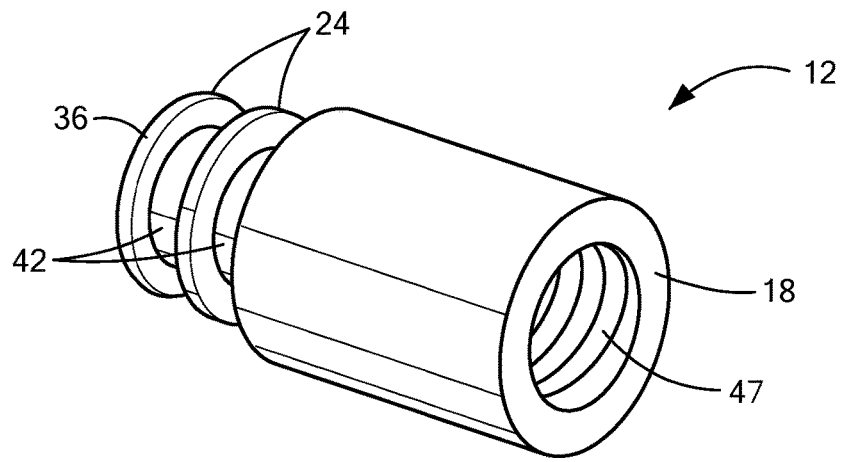
FIG. 3 shows a perspective view of a flanged segment of the adapter device.

As shown in FIG. 2, the device 10 may have a continuous outer diameter, with the outer diameter at the first device end 18, $OD_1$, being the same or at least substantially the same as the outer diameter at the second device end 20, $OD_2$. When the device 10 is in use, however, it will be understood that the flexible conical segment 14 may stretch to fit over an outlet connector (as described in FIG. 6), and this may give the device a larger outer diameter $OD_2$.

Figure 4:
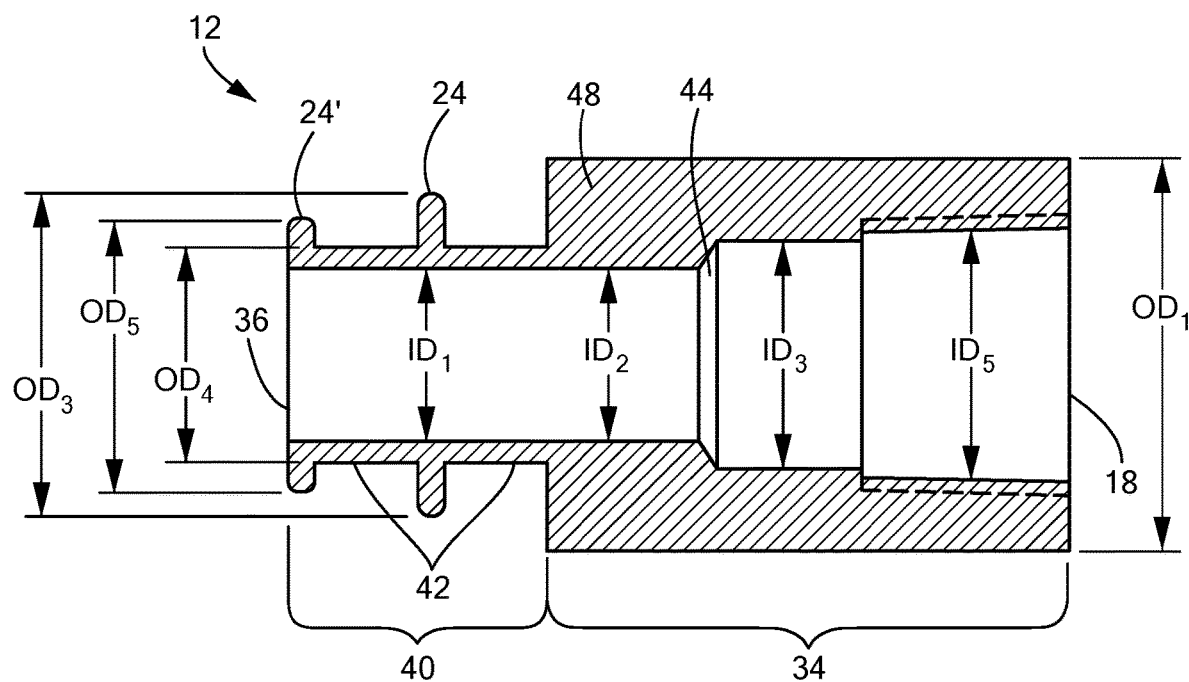
FIG. 4 shows a cross-sectional view of the flanged segment of the adapter device.

As shown in FIG. 4, the flanged segment 12 may include a first portion 34 proximate the first end 18 of the flanged segment 12 and a second portion 40 proximate the second end 36 of the flanged segment 12. The first portion 34 may have a continuous or substantially continuous outer diameter $OD_1$ and the second portion 40 may have a non-continuous outer diameter. The second portion 40 may include one or more flanges 24, at least one of which having a greater outer diameter $OD_3$ than the outer diameter $OD_4$ of the intervening portions 42 between the flanges 24 and between a flange 24 and the first portion 34. As shown in FIG. 4, however, one flange may have an outer diameter $OD_3$ that is greater than the outer diameter $OD_5$ of another flange. For example, a first flange 24' located at the second end 36 of the flanged segment 12 may have a smaller outer diameter than a second flange 24 located proximate the first portion 34 of the flanged segment 12. Further, each flange 24, 24' may have a rounded outer edge (that is, along the outer diameter) that may make the flanges 24, 24' more resistant to breakage.

As shown in FIGS. 2 and 4, the inner surface 46 of the flanged segment 12 may be non-continuous. The inner surface of the second portion 40 may have a continuous or substantially continuous inner diameter $ID_1$, whereas the inner surface 46 of the first portion 34 may have a non-continuous inner diameter. For example, the inner surface of the first portion 34 may include a first inner diameter $ID_2$ that is the same or substantially the same as the inner diameter $ID_1$ of the second portion 40. The inner surface 46 of the first portion 34 may further include a second inner diameter $ID_3$ that is greater than the first inner diameter $ID_2$, a transition area 44 between the first inner diameter $ID_2$ and the second inner diameter $ID_3$ that includes a variable third inner diameter range, and a fourth inner diameter $ID_5$ that is greater than the first inner diameter $ID_2$, second inner diameter $ID_3$, and third inner diameter range of the transition area 44. The inner surface of the second portion 40 may be smooth (that is, not ridged, threaded, textured, or the like). In contrast, at least a portion of the inner surface of the first portion 34 may be threaded 47 to be matably engageable with a compatibly threaded hose, hose component, or other part of the system in which the adapter device 10 is being used. Further, as the outer diameter $OD_1$ of the first portion 34 of the flanged segment 12 is continuous or substantially continuous, the variable inner diameter of the first portion 34 may produce a corresponding increasing thickness of the wall 48 of the first portion 34, with the wall 48 thickness generally increasing from the second end 36 to the first end 18.

Figure 5:
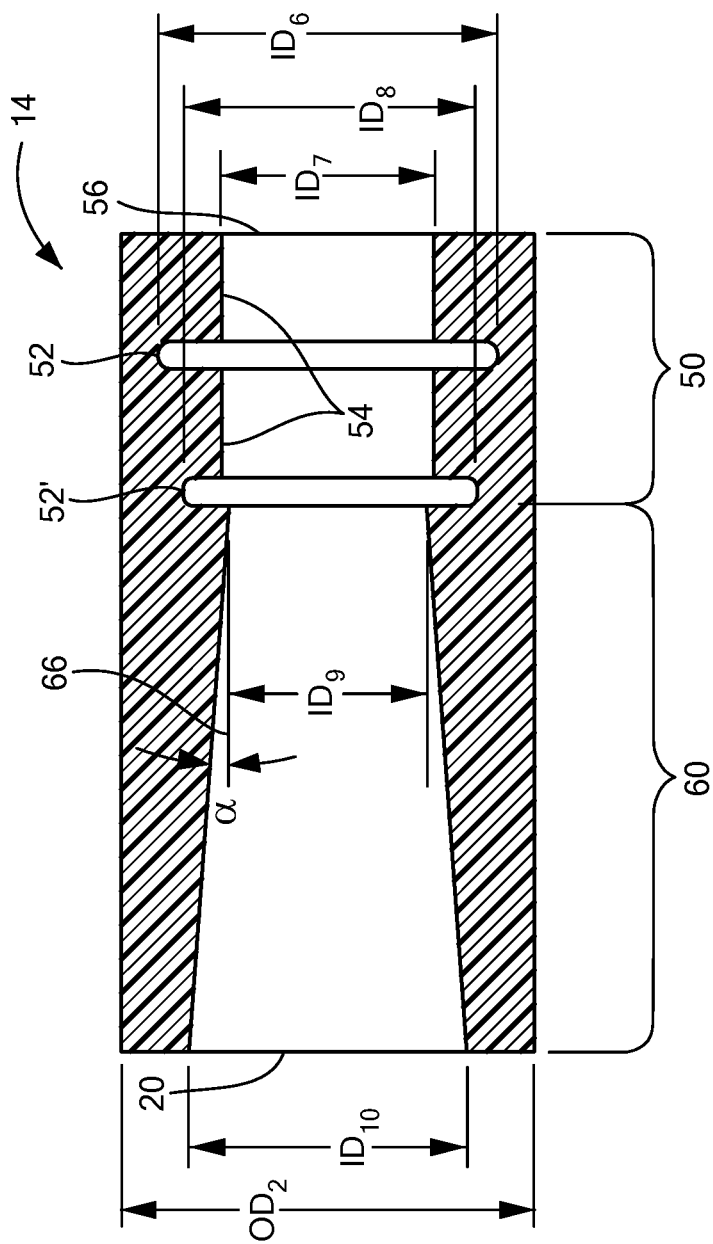
FIG. 5 shows a cross-sectional view of a conical segment of the adapter device.

The conical segment 14 may have a continuous or substantially continuous outer diameter $OD_2$, as shown in FIGS. 2 and 5. In contrast, however, at least a portion of the conical segment 14 may include a non-continuous inner diameter. For example, the conical segment 14 may include a first portion 50 that has an inner surface that is grooved to correspond, both in number and size, to the one or more flanges 24 of the flanged segment 12. In the non-limiting embodiment shown in FIG. 5, the inner surface of the first portion 50 of the conical segment 14 may include two grooves 52 and two intervening portions 54. For example, one intervening portion 54 may be located between the two grooves 52 and the other intervening portion 54 may be located between one of the two grooves 52 and the first end 56 of the conical segment 14. As an example, the inner diameter $ID_8$ of a first groove 52' of the first portion 50 may be the same or substantially the same as the outer diameter $OD_5$ of the first flange 24' and the inner diameter $ID_6$ of the second groove 52 of the first portion 50 may be the same or substantially the same as the outer diameter $OD_3$ of the second flange 24. However, as shown in FIG. 2, the inner diameter $ID_7$ of the intervening portions 54 of the conical segment 14 may be slightly larger than the outer diameter $OD_4$ of the corresponding intervening portions 42 of the flanged segment 12. The conical segment 14 may also include a second portion 60 that has a non-continuous inner diameter, which may be in contact with the flanged segments 12 in the intervening areas when the conical segment 14 and the flanged segment 12 are coupled to each other. For example, the conical segment 14 may be overmolded onto the flanged segment 12.

As shown in FIGS. 2 and 5, the second portion 60 may have an increasing inner diameter, with the inner diameter expanding from a first inner diameter $ID_9$ at the first end 56 of the conical segment 20 toward a second inner diameter $ID_{10}$ at the second end 20 of the conical segment 14. The first inner diameter $ID_9$ may be the same or substantially the same as the outer diameter $OD_4$ of the intervening portions 54 of the intervening portions 42 of the flanged segment 12. Further, the inner diameter of the second portion 60 may increase from the first inner diameter $ID_9$ to the second inner diameter $ID_{10}$ at an angle α of 4° or greater from the horizontal (that is, an imaginary line 66 that extends parallel to the longitudinal axis 22 from the first inner diameter $ID_9$, as shown in FIG. 5). As the outer diameter $OD_2$ of the conical segment 14 may be continuous or substantially continuous, the decreasing inner diameter may produce a corresponding increasing wall thickness in the conical segment 14, with the wall 64 increasing from the second end 20 to the first end 56.

Figure 6:
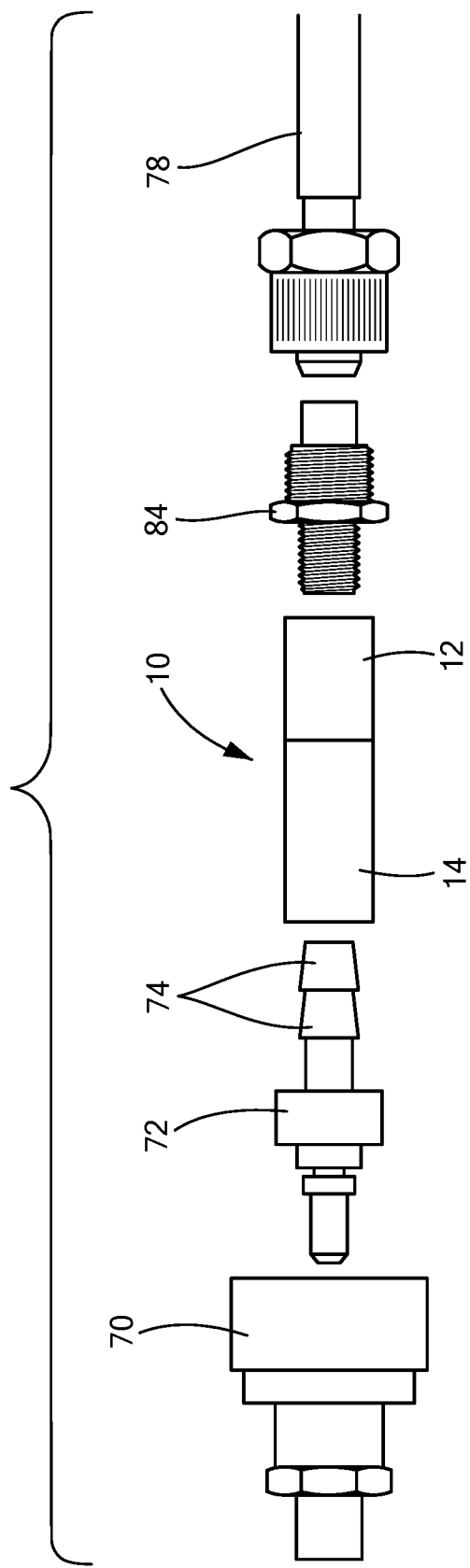
FIG. 6 shows an exploded view of an exemplary use of the adapter device.
Figure 7:
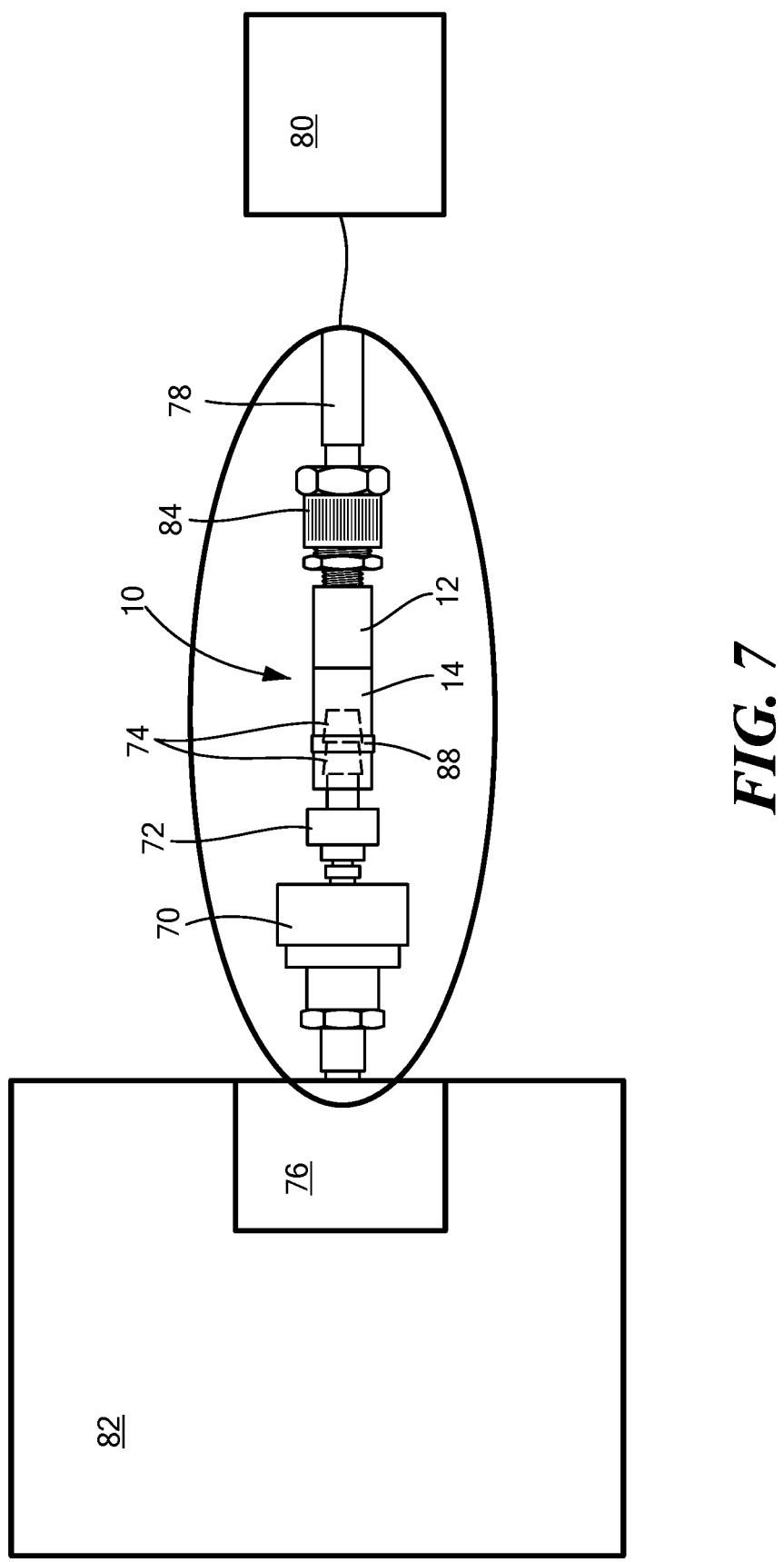
FIG. 7 shows a partially schematic view of an exemplary use of the adapter device.

Referring now to FIGS. 6 and 7, the adapter device is shown in use with an incompatible medical scavenging system. However, this system shown in these figures is merely illustrative, as the adapter may be used in any of a variety of systems, as discussed above. The medical scavenging system shown in FIG. 6 may include a wall connector 70 and a male connector 72 with one or more barbs 74. However, each country or geographic area may use a scavenging system 76 with a different wall connector 70 and/or male connector 72, making it impossible to use a hose 78 from a single cryotreatment system 80 with all scavenging system 76 configurations. In the non-limiting example shown in FIGS. 6 and 7, a standard North American scavenging hose 78 may be used to connect the cryotreatment system 80 to the scavenging system 76 of the medical facility 82. For example, the scavenging system 76 may be located in Asia and, therefore, the wall connector 70 may have a configuration that is standard in that geographic location. The male connector 72 may be compatible with the Asian-configuration wall connection 70, but may be incompatible with the North American-configuration scavenging hose 78 and hose connector 84.

Typically, this combination of incompatible components would mean that the scavenging hose 78 of the cryotreatment system 80 would be unusable with the scavenging system 76 of the medical facility 82. Alternatively, the cryotreatment system 80 would have to be adapted for use in each incompatible geographic location, which would incur great expense and tedious product development, manufacturing, and alteration. However, the adapter device 10 shown and described herein may make it possible to use a standard cryotreatment system 80 (that is, a cryotreatment system that has not been specifically adapted for use) with a scavenging system 76 of any geographic location.

As shown in the inset of FIG. 7, the male connector 72 of the scavenging system 76 may be matably connected with the conical segment 14 of the adapter device 10. Similarly, the hose connector 84 may be matably connected with the flanged segment 12 of the adapter device 10. The conical segment 14 of the adapter device 10 may be composed of a soft, flexible material, such as silicone, that may stretch and bend to accommodate any of a variety of differently sized and/or configured male connectors 72 and barbs 74. Further, the conical inner surface of the conical segment 14 may have a decreasing inner diameter that may securely engage the male connector 72 without slippage or leakage. Optionally, a compression element 88, such as a clamp, tie, elastic band, wrap, clasp, or the like, may be used on the outside of the conical segment 14 to help secure the device 10 to the male connector 72. The compression element 88 may compress or deform the flexible material of the conical segment 14 so that the inner surface of the conical segment 14 is securely in contact with the male connector 72. The hose connector 84 may be secured to the adapter device 10 using the threaded portion of the inner surface of the flanged segment 12. That is, the hose connector 84, which may in turn be connected to the scavenging hose 78 of the cryotreatment system 80, may be screwed into the flanged segment 12. In this way, for example, a North American cryotreatment system 80 and scavenging hose 78 may be securely connected to the scavenging system 76 of any geographic area, regardless of the configuration and/or size of the wall connector 70 and male connector 72.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A universal adapter for a medical system, the universal adapter comprising:
   a first segment having a first portion and a second portion where at least the first portion of the first segment includes a continuous outer diameter, a plurality of inner diameters, the first segment being composed of a rigid material and at least a portion of the first portion of the first segment has a threaded inner diameter, and the second portion of the first segment defines one or more flanges and includes a continuous inner diameter; and a second segment having a first portion and a second portion and being composed of a flexible material, the second segment being coupled to the first segment with at least the first portion of the second segment being disposed about the one or more flanges of the portion of the first segment, the second segment having a single continuous outer diameter that is the same as the continuous outer diameter of the first portion of the first segment.

2. The universal adapter of claim 1, wherein an entirety of the second segment includes a same continuous outer diameter as the continuous outer diameter of the first portion of the first segment such that a portion of the universal adapter has the single continuous outer diameter when the first and second segments are coupled together.

3. The universal adapter of claim 2, wherein the first portion of the second segment abuts the second portion of the first segment.

4. The universal adapter of claim 3, wherein the second portion of the second segment has a tapered inner diameter.

5. The universal adapter of claim 4, wherein the inner diameter of the second portion of the second segment increases from a first end to a second end of the second portion of the second segment.

6. The universal adapter of claim 5, wherein the first portion of the second segment includes a plurality of inner diameters, at least one of the plurality of inner diameters at the first end of the second portion of the second segment being the same as an inner diameter at a second end of the first portion of the second segment.

7. The universal adapter of claim 5, wherein the first portion of the second segment includes a plurality of inner diameters.

8. The universal adapter of claim 7, wherein the first portion of the second segment is at least partially disposed about the one or more flanges of the first segment.

9. A universal adapter for a medical system, the universal adapter comprising:

a first segment having a first portion and a second portion where the first portion of the first segment includes a continuous outer diameter, a plurality of inner diameters, and at least a portion of the first portion of the first segment has a threaded inner diameter and the second portion includes a continuous inner diameter and defines one or more flanges, the first segment being composed of a rigid material; and a second segment composed of a flexible material having a first portion and a second portion, the first portion and the second portion of the second segment each including a plurality of inner diameters, the second segment being coupled to the first portion of the first segment with at least a portion of the second segment being disposed about the one or more flanges of the first segment, the second segment having a single continuous outer diameter that is the same as the continuous outer diameter of the first portion of the first segment.

10. The universal adapter of claim 9, wherein the first portion of the second segment abuts the second portion of the first segment.

11. The universal adapter of claim 10, wherein the second portion of the second segment has a tapered inner diameter.

12. The universal adapter of claim 9, wherein each of the first segment and the second segment defines a passage therethrough.

13. A universal adapter for a medical system, the universal adapter comprising:

a first segment having a first portion and a second portion where the first portion of the first segment includes a continuous outer diameter, a plurality of inner diameters, and at least a portion of the first portion of the first segment has a threaded inner diameter, and the second portion of the first segment includes a continuous inner diameter and defines one or more flanges, the first segment being composed of a rigid material; and a second segment composed of a flexible material having a first portion and a second portion, the first portion and the second portion of the second segment each including a plurality of inner diameters, the second portion of the second segment having a tapered inner diameter, the second segment being coupled to the first portion of the first segment with at least a portion of the second segment being disposed about the one or more flanges of the first segment, the second segment having a single continuous outer diameter that is the same as the continuous outer diameter of the first portion of the first segment, the first portion of the second segment abutting the second portion of the first segment.

* * * * *